(12) United States Patent  (10) Patent No.: US 8,173,421 B2
Kitta et al.  (45) Date of Patent: May 8, 2012

(54) ARRANGEMENT FOR TRANSPORT AND/OR SAFEKEEPING OF A HUMAN OR ANIMAL TISSUE SAMPLE

(75) Inventors: Johann Karl Kitta, Waldbröl-Herfen (DE); Abdolhamid Huschmand Nia, Pitmasens (DE)

(73) Assignee: Klinica Medical GmbH, Usingen (DE)

( * ) Notice: Subject to any disclaimer, the term of this patent is extended or adjusted under 35 U.S.C. 154(b) by 0 days.

(21) Appl. No.: 12/995,449

(22) PCT Filed: May 25, 2009

(86) PCT No.: PCT/EP2009/056320
§ 371 (c)(1),
(2), (4) Date: Jan. 17, 2011

(87) PCT Pub. No.: WO2009/144202
PCT Pub. Date: Dec. 3, 2009

(65) Prior Publication Data
US 2011/0104797 A1  May 5, 2011

(30) Foreign Application Priority Data
May 31, 2008 (DE) .................... 20 2008 007 356 U
Aug. 5, 2008 (DE) .................... 20 2008 010 411 U

(51) Int. Cl.
*C12M 1/00* (2006.01)
(52) U.S. Cl. ............... 435/307.1; 435/284.1; 422/536; 422/563
(58) Field of Classification Search .......... 435/40.5, 435/40.52, 284.1, 307.1; 422/536, 546, 551, 422/570, 560, 561, 563; 428/99, 100; 378/208
See application file for complete search history.

(56) References Cited

U.S. PATENT DOCUMENTS

| 4,721,644 | A | * | 1/1988 | Mayo ............................ 428/91 |
| 5,002,735 | A | | 3/1991 | Alberhasky et al. |
| 5,733,612 | A | * | 3/1998 | Garry ............................ 428/23 |
| 2008/0299605 | A1 | * | 12/2008 | Lary et al. .................... 435/40.5 |

FOREIGN PATENT DOCUMENTS
DE  202009013353  12/2009
(Continued)

OTHER PUBLICATIONS

International Search Report for related International Application No. PCT/EP2009056320 dated May 12, 2010 (4 pages).
International Preliminary Report on Patentability for related International Application No. PCT/EP2009056320 dated Nov. 30, 2010 (6 pages).
Written Opinion of the International Searching Authority for related International Application No. PCT/EP2009056320 dated Nov. 30, 2010 (5 pages).

*Primary Examiner* — William H Beisner
*Assistant Examiner* — Michael Hobbs
(74) *Attorney, Agent, or Firm* — Margaret Polson; Oppedahl Patent Law Firm LLC

(57) ABSTRACT

An arrangement for the transport and/or safekeeping of a human or animal tissue sample comprising a tablet and one or more alignment pins; each pin having a tip to pierce the cover of the tablet; the tablet designed with at least two layers that include a cover layer and a support member; and at least one alignment pin with a tip that is undercut in the direction of piercing so that it locks against the inside of the cover layer, counteracted by a lower piercing resistance of the support member in the area the piercing point. Upon piercing the cover layer, the tablet and/or the respective alignment pin limit the piercing depth of the alignment pin forming a locking event. The arrangement is designed to preserve orientation information and allow for unobscured imaging of the sample.

17 Claims, 2 Drawing Sheets

| | FOREIGN PATENT DOCUMENTS | | WO | 2006092797 | 9/2006 |
|----|----|----|----|----|----|
| WO | 0049447 | 8/2000 | | | |
| WO | 02059571 | 8/2002 | * cited by examiner | | |

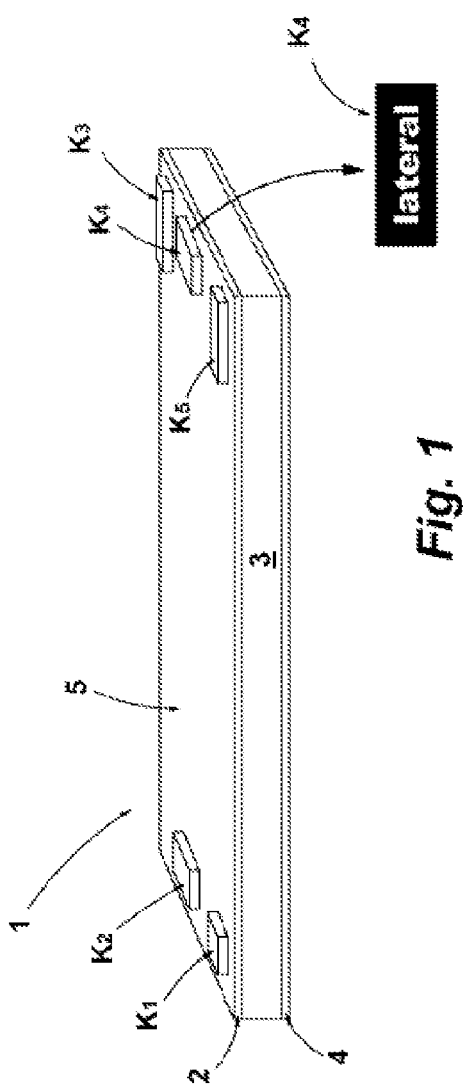
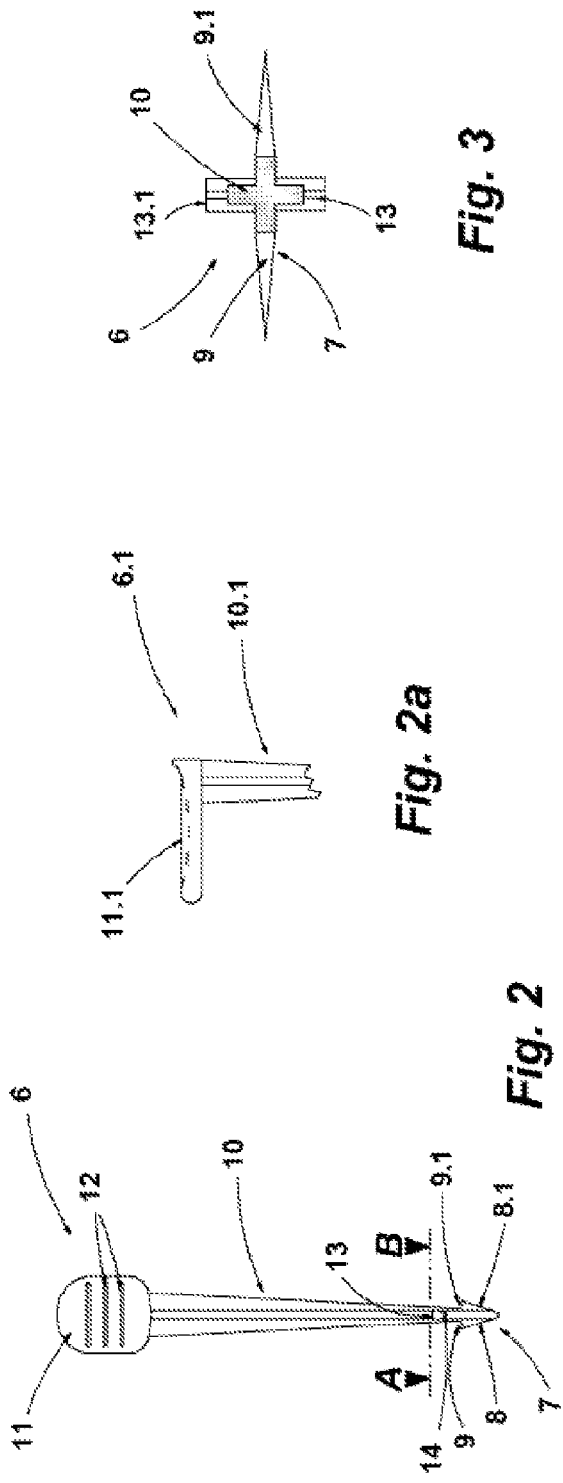

ARRANGEMENT FOR TRANSPORT AND/OR SAFEKEEPING OF A HUMAN OR ANIMAL TISSUE SAMPLE

CROSS REFERENCE APPLICATIONS

This application is a national stage entry of PCT/EP2009/056320 filed May 5, 2009 which claims priority from German application number 20 2008 007 356.1 filed May 31, 2008 and German application number 20 2008 010 411.4 Aug. 5, 2008.

FIELD OF THE DISCLOSURE

The subject matter of the invention is an arrangement for the transport and/or the storage of a human or animal tissue sample comprising a tray and one or more alignment pins for fixing the tissue sample on the tray, each of said pins having a tip for inserting the pins into the tray.

BACKGROUND

Tissue removed by surgery from a human or animal body, such as a tumor, is normally subjected as a tissue sample to further examination. Fine tissue examinations of this type are usually performed by a pathologist. It is particularly important that if such tissue sample involves a malignant tumor to determine within the scope of such examination whether the tumor was actually completely removed. A tumor is considers completely removed if a safety border of healthy tissue exists around the tumor that was removed. If such tumor did not have a sufficient safety border, the surgeon also needs to know on which side of the tumor there is an insufficient safety border, so that post-resection can be performed at this location. For this purpose it is necessary that the orientation of the removed tissue sample from within the body is documented and retained.

Currently, different methods are used to mark the removed tissue sample with respect to its orientation in the body. Sometimes this is performed by introducing various threads into the tissue sample to mark which side of the removed tissue corresponds to a particular orientation in the body. Sometimes color markings are also applied on the sample itself. Besides the fact that such markings are inadequate, because reliable orientation is not possible, the marking of the sample itself also has the disadvantage that such markings are visible on x-ray images and therefore can impair the diagnosis. This is undesirable, since such superimposition on images can impair the diagnosis or even falsify it.

When marking the tissue samples themselves, another important aspect is arranging proper transportation and/or the storage of tissue samples.

According to another embodiment of the device for the transport of tissue samples, cork sheets are used onto which the tissue samples are attached with steel cannulas that are available as standard equipment in operating theaters. The steel cannulas are pushed through the removed tissue sample and fixed in the cork sheet. The cork sheet is subsequently marked with information on the orientation of the removed tissue samples in the body. The use of steel cannulas is not without problems. Such steel cannulas have a very sharp tip which can cause considerable injuries to the persons handling such sample, including the risk of infection. The tip of the cannula can even project on the lower side of the cork sheet, which happens quite frequently. The cannula canal can also contain tissue sample material. Additionally, the steel cannulas have the risk that they can slide out of the cork sheet during the transportation of the tissue sample which results loosing the information on the orientation of the tissue sample. In order to obtain an x-ray image that can be analyzed, the tissue sample must be removed from the cork sheet, since such sheet cannot be x-rayed homogenously. Such sheet produces shadows or can also produce lighter areas or lines in the x-ray image.

A tray for transporting and for the storage of tissue samples is known from U.S. Pat. No. 4,993,056 A, in which the tissue sample is clamped between two panels of a tray. The one panel has an x-ray-opaque grating as coordinate system. With such a tray, the tissue sample cannot be readjusted. Because of its relatively high production cost, this tray is designed for multiple uses and must therefore be cleaned and disinfected after each use, which is time-consuming and cost intensive. In addition, if such tray is used, x-ray pictures cannot be made in a vertical direction. Additionally to clamp a tissue sample between two panels for transportation over extended distances is unsuitable. Transportation in formaldehyde is also not possible using this tray, since there is insufficient contact with the formaldehyde due to the clamping of the sample.

The foregoing example of the related art and limitations related therewith are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tool and methods which are meant to be exemplary and illustrative, not limiting in scope. In various embodiments, one or more of the above described problems have been reduced or eliminated, while other embodiments are directed to other improvements.

Based upon the previously discussed prior art, an aspect of the invention is therefore to further develop the arrangement mentioned at the outset in such a way that the disadvantages that most closely resemble those indicated in the prior art are at least partially prevented.

The invention teaches that this problem is solved by a generic arrangement named at the outset, in that the tray is designed with at least two layers and comprises a cover layer with a top side provided for attaching the tissue sample as well as a support body connected with the cover layer, the at least one alignment pin has a tip that is undercut in the direction of piercing, the undercut of which bears against the inside of the cover layer for locking the alignment on the tray after sticking said alignment pin into the tray, a lower counter pressure counteracts at least in the area of an intended incision point against the tip of an alignment pin during the incision through the support body than during the incision into the cover layer, and the tray and/or the respective alignment pin for developing a latch have means to limit the piercing depth of the alignment pin into the tray.

In this arrangement for the transport and/or the storage of a human or animal tissue sample, specific alignment pins are used for fixing a surgically removed tissue sample on the tray. The tray itself is designed with two layers and comprises an upper cover layer, the top side of which is for attaching the tissue sample, and a support body below it which is connected with the cover layer. In this context, it is stipulated that the cover layer itself and the support body below it provide a different piercing counter pressure to an alignment rod to be anchored in it in each case, where the incision counter pressure for pushing-through the alignment pin by means of its tip through the cover layer is larger than the incision counter pressure that is provided by the support body.

By interaction with this contrast in incision counter pressure between the cover layer and the support body, it is possible to anchor the alignment pin in the tray by providing an undercut tip having one or more barbs through its undercut. The tip of the alignment pin is pushed through the cover layer completely, which is the stipulated requirement for anchoring an alignment pin in the tray, where the barbs and/or the undercut serve for locking the alignment pin in the cover layer of the tray. Consequently, in order to lock an alignment pin in the tray, the barb(s) bear(s) against the inside of the cover layer. The cover layer can be placed into the undercut by the conditional restoring force of the material after the piercing by tip. In the preferred embodiment the alignment pin has a flat tip, so that the at least one barb protrudes in the radial direction and after turning the alignment pin, the barb engages through the incision behind an undamaged section of the cover layer. This lock is designed as a quarter-turn lock. The support body of the tray is designed so that in case of such quarter-turn like locking of the alignment pin, it is not restored into its incision position through the elasticity of the support body.

Either the tray or the respective alignment pin has means for limiting the piercing depth of the alignment pin to prevent the alignment pin from being pushed through the tray. The alignment pin can comprise, one or several projections at a distance to the undercut formed by the tip acting in a radial direction with a stop pointing toward the tip as the means for limiting such piercing depth. During the process of pushing the tip of the alignment pin through the cover layer, this projection acts as a stop, as a result of which any further piercing by application of the designated forces is prevented, in principle. By providing a flat tip with such alignment pin, the projection preferably also has a flat form, where the plane of the at least one projection is arranged at an angle to the plane of the tip. Then the projection limiting the piercing depth impinges on the top side of the cover layer transverse to the incision by the tip.

Instead of or in addition to one or more radial projections with the alignment pins used to limit piercing depth, the tray can also comprise a lower cover layer, which cannot or at least cannot easily be penetrated by the tip of the alignment pin.

Ultimately, any element that has the above-mentioned characteristics, could be used as a support body. For that reason, it is possible to apply the cover layer on a cartridge or frame type support body, in principle, where the area of the planned incision(s) is/are provided for fixing the alignment pins on the tray in an area without a frame. Such frame ultimately serves to provide a latching cavity as well as for stiffening the cover layer.

In the event that the tray has characteristics suitable for x-rays, in particular those that make it possible to x-ray the tray without producing shadow effects or suchlike, it was surprisingly found that the use of a normal commercial PUR rigid foam panel is particularly suited for these purposes. Such rigid foam panel not only grants the tray the necessary stability and ensures appropriate designated anchoring of the alignment pin(s) in the cover layer applied thereon, but, most likely due to the homogeneity of the material and the stipulated thickness of same, it can be utilized for radiographic imaging of the tissue sample, for instance of the tumor, without impairing the imaging quality. Furthermore, it was again surprisingly found that during the use of such panel as a support body of a tray also other imaging examinations could be performed on the tissue sample attached to the tray, such as sonographic examinations, without the tray impairing the result, and that the tissue sample therefore does not have to be removed from the tray for such examinations.

An arrangement for the transport and/or the storage of a human or animal tissue sample as previously described can be produced economically. The tray can therefore consist of a sandwich panel designed for other purposes, which has a PUR rigid foam core and a cover layer from pulp cardboard that is plastic-coated on both sides, for example.

The alignment pins preferably consist of a plastic material, in particular of fiber-reinforced plastic, and are typically produced by injection molding. The manufacturing costs of such arrangement can be regarded as being relatively low, with the consequence that such arrangement is particularly suited for producing single-use arrangements and/or disposable arrangements. In addition, this has the advantage that the entire arrangement with the tissue sample fixed thereon can all be disposed of together. The removal of same for continued use of the tray, including appropriate disinfection, is therefore not necessary.

With the arrangement described, it is easily possible to provide identification marks on the cover layer, such as marks to indicate the orientation of the tissue sample in the human or animal body. Such identification marks are preferably designed to be radiographic opaque so that they are visible in the x-ray image. Such identifiers can be created by imprinting of lettering with a radiographic opaque printing medium, or by the application of identification elements. If identification elements are provided, these can also be designed as plastic injection moldings, which can be bonded to the cover layer. Is also possible to arrange one or more interlock extensions on the rear of such identification element. The fixing on the tray is then done by simply by pressing same into the cover layer of the tray. With such embodiment it is possible to provide the tray with the corresponding identification marks preassembled to an operator or to give the operator the opportunity to apply the orientation identification marks himself after fixing the tissue samples on the tray.

In addition to the exemplary aspects and embodiments described above, further aspects and embodiments will become apparent by reference to the accompanying drawings forming a part of this specification wherein like reference characters designate corresponding parts in the several views.

BRIEF DESCRIPTION OF THE DRAWINGS

FIG. 1: is a schematic perspective view of a tray for an arrangement for the transport and/or the storage of a human or animal tissue sample.

FIG. 2: is a side elevation of an alignment pin for fixing a tissue sample on the tray of FIG. 1.

FIG. 2a: is a section of a further alignment pin on the side of the handle for fixing a tissue sample on the tray of FIG. 1, FIG. 3: is an enlarged sectional view through the alignment pin of FIG. 2 along the A-B line.

Figure 5:
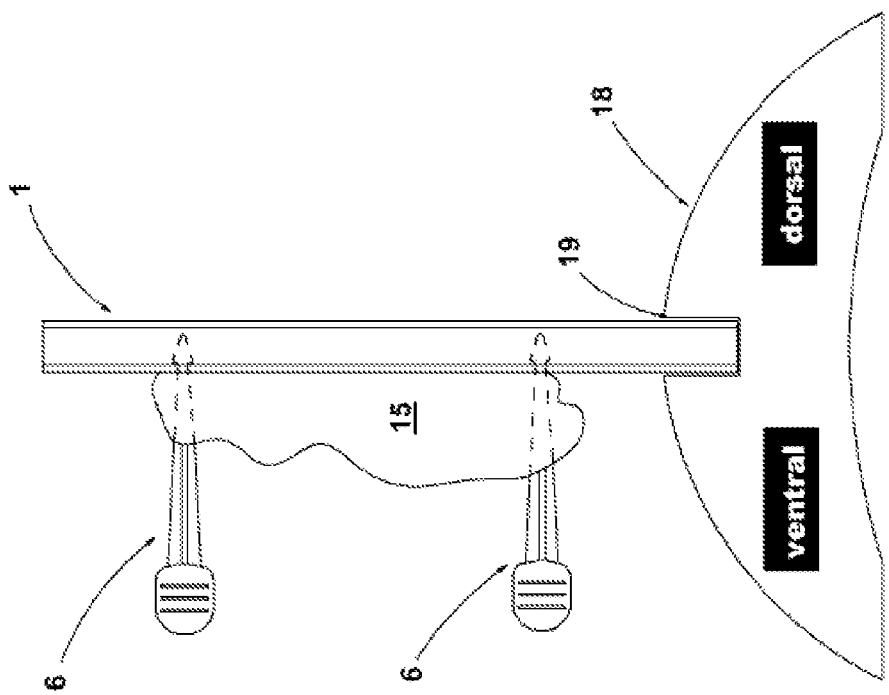

Before explaining the disclosed embodiment of the present invention in detail, it is to be understood that the invention is not limited in its application to the details of the particular arrangement shown, since the invention is capable of other embodiments. Exemplary embodiments are illustrated in referenced figures of the drawings. It is intended that the embodiments and figures disclosed herein are to be considered illustrative rather than limiting. Also, the terminology used herein is for the purpose of description and not of limitation.

DETAILED DESCRIPTION OF THE DRAWINGS

A tray 1 is part of an arrangement for the transport and/or the storage of a human or animal tissue sample. The tray 1 of the illustrated embodiment is designed with a sandwich construction and has an upper cover layer 2, a polyurethane rigid foam panel as support body 3, and a lower cover layer 4. In the depicted embodiment, the two cover layers 2, 4 are plastic-coated pulp cardboard layers with a thickness of approximately 0.5 mm. The support body 3, is a normal commercially available PUR rigid foam panel with a more than 95% closed-cell structure. The pore size of the rigid foam is small and preferably does not exceed an average pore size of 0.2 to 0.4 mm. The rigid foam property has only a small elastic restoring rate. The rigid foam can be cut into without problems. The thickness of the tray represented in FIG. 1 is 10 mm.

The top side 5 of the upper cover layer 2 of the tray 1 is used for fixing a tissue sample. In order to mark the orientation of the tissue sample to be attached onto the top side 5 of the tray 1, several markings $K_1$-$K_5$ are affixed on the top side 5 of the upper cover layer 2.

With the identification mark $K_1$ this involves an "L" and/or an "R," which stands for right ("R") and/or left ("L"). The identification marks $K_2$-$K_5$ indicate the orientation of the removed tissue sample within the body. In the represented embodiment, the identification mark $K_2$ stands for "medial," the identification mark $K_3$ for "cranial," the identification mark $K_4$ for "lateral," and the identification mark $K_5$ for "caudal." The tissue sample is fixed on the top side of the tray 1 according to the specified orientation of the represented exemplary embodiment. The identification marks $K_1$-$K_5$ are plastic components that are attached on the tray 1 as described in connection with FIG. 4, and into which the respective orientation is inserted as a recess. The plastic material of the identification marks $K_1$-$K_5$ is radiographic opaque, so that the writing inserted therein is identifiable in the x-ray image. By way of an example, the identification mark $K_4$ in FIG. 1 is additionally shown as a horizontal projection. The identification marks $K_1$-$K_5$ are arranged outside of the area of the top side 5 of the tray into which the tissue sample is to be placed as represented in FIG. 1. It is advantageous, if the identification marks $K_1$-$K_5$ are applied such that a tissue sample that is fixed on the tray 1 can also be x-rayed in a cranial-caudal direction, without that the identification marks $K_1$-$K_5$ can be noticeable as shadows. For this reason, the identification marks $K_3$ and $K_5$ are along the right side of the tray 1 and are therefore arranged outside of the said x-ray direction.

The tray 1 is sufficiently dimensionally stable because of the materials used and the sandwich construction. Likewise, the tray 1 is resistant to formaldehyde, which is required for the storage of tissue samples.

Several alignment pins are used for fixing a tissue sample on the tray 1. FIG. 2 shows a side view of an embodiment of such an alignment pin 6. The alignment pin 6 is an injection molding and consists of a hard plastic, which is fiber-reinforced in the depicted embodiment. The alignment pin 6 has a flat tip 7, which has two cutting edges 8, 8.1 for piercing the said alignment pin through a tissue sample and for piercing the upper cover layer 2 of the tray 1. The tip 7 is undercut forming a barb. In FIG. 2, the edges of the tip 7 forming the undercut are marked with the reference symbol 9, 9.1.

A shaft 10 is molded onto the tip 7. The shaft 10 has a cruciform cross-sectional area, as can be seen from the sectional view of FIG. 3. The shaft 10 is designed conical overall, tapering in the direction toward the tip 7. A handle 11 is molded onto the upper end of the shaft 10. The flat sides of the handle 11 are characterized by bosses 12 to increase the gripability of the handle 11. In the depicted embodiment, the alignment of the handle 11 follows the longitudinal extension of the shaft 10. FIG. 2a shows an alternative embodiment of an alignment pin 6.1, in which the handle 11.1 is arranged right-angled to the shaft 10.1 from which it protrudes in one direction. The handle 11.1 is troughed on its top side (dotted line). This handle 11.1 can be pushed with the thumb through the tissue sample to be fixed into the tray by applying the necessary compressive force. A further embodiment that is not represented in the Figures concerns an arrangement of the handle to the shaft, in which the handle is seated centrally on the shaft of the alignment pin, similar to a pan head.

At a distance from the tip 7, two projections 13, 13.1 from longitudinal axis of the shaft 10 are molded onto the shaft 10 and are diametrically opposed to each other. The projections 13, 13.1 function as limiting means for the piercing depth of the alignment pin 6 to limit the piercing depth of the tip 7 into the tray 1. As can be seen from the cross-sectional view of FIG. 3, the tip 7 is designed as a flat tip. The plane of the projections 13, 13.1 is arranged at a right-angle to the plane of the tip 7. The projections 13, 13.1 taper in direction of the tip 7 and on their lower side have a blunt limit stop edge 14. The width of the projections 13, 13.1 is adjusted in the radial direction such that the piercing through the tissue sample to be fixed is not or not noticeably impeded, but at the same time they represent an effective limit stop during the process of inserting the alignment pin 6 into the upper cover layer 2 of the tray 1.

A tissue sample is fixed on the tray 1 typically with at least two or even several alignment pins.

At least two alignment pins 6 are necessary for fixing when a tissue sample is to be oriented on the tray 1, which should normally be the case. The shaft of the alignment pins can have a different length so that longer or also shorter alignment pins can be used for fixing same on the tray depending on the thickness of the tissue sample to be mounted.

Figure 4:
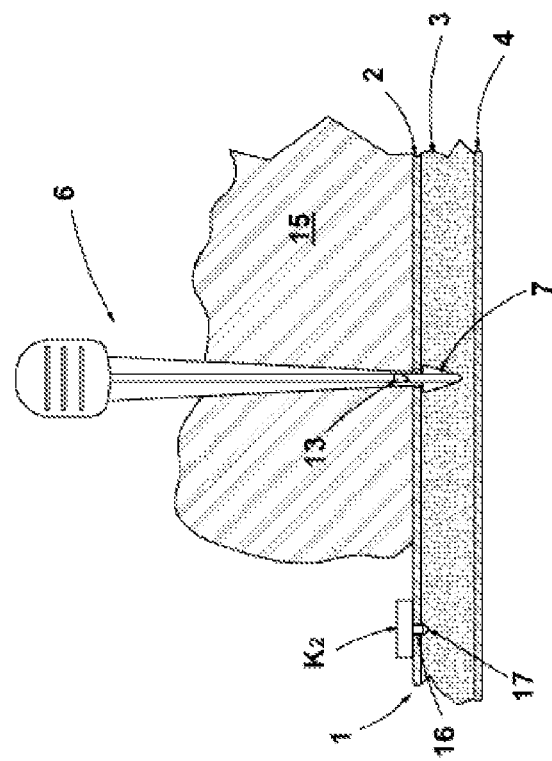
FIG. 4: is a schematic sectional detail view through a tissue sample that is fixed on the tray of FIG. 1 by means of alignment pins in a section pursuant to FIG. 2, and FIG. 5: is the arrangement of FIG. 4 supported in a stand.

FIG. 4 illustrates a tissue sample 15 that is fixed with several alignment pins 6 on the tray 1, as a sectional detail view. The tissue sample 15 with respect to its orientation in the body, from which it was removed is placed onto the top side of the upper cover layer 2 of the tray 1. Then the alignment pin that can be seen in FIG. 4 is pushed through the border of the tissue sample 15 and with its tip 7 through the upper cover layer 2 and into the carrier element 3 formed by the PUR rigid foam panel. This piercing process is limited by the projections 13, 13.1 that are offset at an angle to the cutting edges 8, 8.1 of the tip 7, as these function on the top side of the upper cover layer 2 as a stop limit. The angular offset arrangement of the projections 13, 13.1 to the plane of the tip 7 is advantageous, because the projections 13, 13.1 are reaching a section of the upper cover layer that has not been damaged by the cutting edges 8, 8.1 for placement and therefore effectively complete the piercing process. The operator who is fixing the tissue sample is transmitted a haptic response as a result of the sudden increase in the piercing counter pressure that the designated piercing depth of the alignment pin 6 into the tray 1 has been reached through the projections 13, 13.1 serving as stop limit. The length of the tip 7 has a shorter dimension than the thickness of the support body 3. The distance of the projections 13, 13.1 from the undercut 9, 9.1 of the tip 7 is sufficient such that the upper cover layer 2 can fit into the latch formed by the undercut 9, 9.1 and the projections 13, 13.1. One will typically provide a corresponding distance to allow a certain clearance by taking into account the thickness of the cover layer 2. In this context it is provided that the distance of the limit stop edges of the projections 13, 13.1 of the front end of the tip 7 is smaller than the thickness of the support body 3.

After the insertion of the tip 7 into the support body 3, the alignment pin 6 is rotated by approximately 90° so that the edges 9, 9.1 forming the undercut for locking the alignment pin 6 during the piercing of the sections that are undamaged by the cutting edges 8, 8.1 acting against the upper side of the top cover layer 2 of the tray 1. The insertion of the tip 7 and the piercing of same through the upper cover layer 2 and the subsequent rotation of the plane of the tip 7 around its longitudinal axis from its position of insertion into a position of locking permits the lock to be described as being similar to a bayonet. FIG. 4 shows the alignment pin 6 in a position that is rotated by 90° with respect to the orientation of penetration which locks the tip 7.

With the identification marks $K_1$-$K_5$, this involves radiographic opaque plastic nameplates, which comprise one or several interlock extensions 16, as it can be seen using the identification mark $K_2$ in FIG. 4. The interlock extensions 16 include a locking head 17 which forms an undercut into which the upper cover layer 2 enters after piercing the interlock extension 16 through the upper cover layer 2, because of its material-based restoring force.

One or more stands for supporting the tray 1 with a tissue sample 15 that is fixed on it can be provided. Part of a stand is shown as an example together with the tray 1 and the tissue sample 15 fixed on it with two alignment pins 6 and is marked with the reference symbol 18 in FIG. 5. The complete stand 18 normally consists of two similar stands arranged parallel to each other. Each stand has a recess 19 on the top side for inserting an edge section of the tray 1. The stands 18 serve for setting up the tray 1, in the event that radiological examinations are to be performed on the tissue sample 15 in a specific spatial position that deviates from the horizontal. In the illustrated embodiment of the stands 18, the recess 19 is at a right angle to the horizontal. Different stands can be provided which comprise recesses with a different degree of inclination with respect to the horizontal, for example recesses with an inclination of 30, 45, or 60°.

The stand 18 can consist of the same sandwich panel material as the tray. The stands 18 are preferably labeled, in order to recognize the orientation of the tissue sample. For this purpose, labeling such as "ventral" (front) and "dorsal" (rear) is suitable. For the use of a stand, these types of identification marks can be designed from the material same as the tray, like the identification marks $K_1$-$K_5$.

The tray 1 as well as the alignment pins 6 can be produced economically. With the aforementioned arrangements for the transport and/or the storage of the human or animal tissue sample this typically involves a disposable arrangement, so that this can be disposed of together with the tissue sample that is no longer required.

The properties of the tray described, in particular by use of the PUR rigid foam layer and/or panel used as the support body 3 and the described locking of the tissue samples on the top side of the upper cover layer, allows that the tray 1 to be used as a float. This allows the tissue sample to be stored in an overhead arrangement, immersed into formaldehyde. This facilitates the neat insertion and removal of the tissue sample from a formaldehyde bath. For this purpose, the lower cover layer 4 can have tab-like extensions, which serve as handle when they are bent open for inserting and removing the tray 1 into a formaldehyde bath with a tissue sample 15 fixed on it in an overhead arrangement, In this arrangement the tissue sample is at the very bottom and the tray 1 is at the very top.

The foregoing description of the invention represents an exemplary embodiment of the invention. Without leaving the scope of the claims, numerous further developments can be deduced by a person skilled in the art who is active in this field, taking into account these embodiments.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

LIST OF REFERENCE SYMBOLS

1 Tray
2 upper cover layer
3 Support body
4 lower cover layer
5 top side
6, 6.1 Alignment pin
7 Tip
8, 8.1 Cutting edge
9, 9.1 Undercut
10, 10.1 Shaft
11, 11.1 Handle
12 Boss
13, 13.1 Projection
14 Limit stop edge
15 Tissue sample
16 Interlock extension
17 Locking head
18 Stand
19 Recess
$K_1$-$K_5$ identification marks

The invention claimed is:

1. A kit for the transport and storage of a human or animal tissue sample comprising:
   a tray and at least one pierceable alignment pins having a tip for fixing the tissue sample on the tray;
   the tray having at least two layers, a cover layer and a support body; the cover layer having a top side for attaching the tissue sample; the support body connected to the cover layer;
   at least one alignment pin having a tip that is undercut in the opposite direction of piercing, the undercut locking the alignment pin on the tray by bearing against the inside of the cover layer after sticking said alignment pin into the tray wherein the pin is adapted to bring the undercuts against the inside of the cover layer when the pin is turned;
   wherein the cover layer has a first piercing counterpressure at the designated insertion point of an alignment pin and wherein the support body has a second piercing counterpressure at said designated insertion point, said second piercing counterpressure being lower than said first piercing counterpressure; and a means to limit the piercing depth of the alignment pin into the tray.

2. The kit of claim 1 wherein the means to limit the piercing depth of the alignment pin into the tray comprises at least one projection from the pin in a radial direction at a distance from the undercut.

3. The kit of claim 1 wherein the tray further comprises a second cover layer arranged on the opposite side of the cover layer that is connected with the support body whereby the piercing depth of the alignment pin is limited.

4. The kit of claim 2 wherein the tip of the alignment pin is in the form of a flat tip.

5. The kit of claim 4 wherein the at least one radial projection is flat and a plane of the projection is arranged at an angle, in particular at a right angle to the plane of the tip.

6. The kit of claim 1 wherein the at least one alignment pin is a plastic component, in particular a fiber-reinforced plastic component.

7. The kit of the claim 1 wherein the at least one alignment pin further comprises a handle.

8. The kit of claim 7 wherein the handle is angled relative to a longitudinal extension of the shaft of the alignment pin.

9. The kit of claim 1 wherein the cover layer of the tray is a plastic-coated pulp cardboard layer.

10. The kit of claim 1 wherein the support body of the tray is a material support layer of homogenous material.

11. The kit of claim 10, wherein the support body is a rigid foam layer.

12. The kit of claim 11, wherein the rigid foam layer is a PUR rigid foam layer.

13. The kit of claim 1 wherein the cover layer has orientation identification marks on its top side for orienting and attaching the tissue sample on the tray.

14. The kit of claim 13, wherein the orientation identification marks in the cover layer of the tray are anchorable plastic components.

15. The kit of claim 13, wherein orientation identification marks are visible (radiographic opaque) in an x-ray image.

16. The kit of claim 1 further comprising at least one stands for setting up the tray.

17. The kit of claim 1 whereby the alignment pins preserve orientation of the tissue and the tray superimposes no markings or distortions on x-ray images of the tissue.

* * * * *